United States Patent [19]

Ikawa et al.

[11] Patent Number: 4,491,668
[45] Date of Patent: Jan. 1, 1985

[54] PROCESS FOR PREPARING L-ASCORBIC ACID

[75] Inventors: Kenji Ikawa; Kanji Tokuyama, both of Osaka; Masumi Kiyokawa, Hyogo, all of Japan

[73] Assignee: Shionogi & Co., Ltd., Osaka, Japan

[21] Appl. No.: 477,925

[22] Filed: Mar. 23, 1983

[30] Foreign Application Priority Data

Apr. 9, 1982 [JP] Japan ................... 57-60121

[51] Int. Cl.$^3$ .......................................... C07D 307/62
[52] U.S. Cl. .................................................... 549/315
[58] Field of Search .......................................... 549/315

[56] References Cited

U.S. PATENT DOCUMENTS 2,129,317  9/1938  Elger .................................... 549/315
2,179,978  11/1939  Elger .................................... 549/315
2,462,251  2/1949  Bassford et al. ..................... 549/315

FOREIGN PATENT DOCUMENTS 164552  11/1949  Austria ................................. 549/315
684725  12/1939  Fed. Rep. of Germany ....... 549/315
86627   12/1971  German Democratic Rep. .................................... 549/315
1222322  2/1971  United Kingdom ................ 549/315

Primary Examiner—Norma S. Milestone
Attorney, Agent, or Firm—Birch, Stewart, Kolasch & Birch

[57] ABSTRACT

L-ascorbic acid is prepared from sodium 2-keto-L-gulonate by introducing gaseous hydrogen chloride in a molar ratio of about 1.5-2.0 to the sodium-2-keto-L-gulonate into a mixture composed of the sodium 2-keto-L-gulonate, ethanol and acetone at a ratio of 1:0.25-1.00:0.5-2.5 by weight at a temperature of about 25°-75° C. until precipitation of sodium chloride ends, removing the precipitated sodium chloride before L-ascorbic acid begins to crystalize out, maintaining the filtrate or supernatant at a temperature of about 25°-75° C. for a period of 5-100 hours and cooling it to yield crystals of L-ascorbic acid as a final product. A solvent inert to the L-ascorbic acid and 2-keto-L-gulonate may be added to the filtrate or supernatant with a favorable result in obtaining purer intended product.

4 Claims, No Drawings

PROCESS FOR PREPARING L-ASCORBIC ACID

BACKGROUND AND FIELD OF THE INVENTION

The present invention relates to a process for preparing L-ascorbic acid (hereinafter, referred to as ASA) from sodium 2-keto-L-gulonate (hereinafter, referred to as Na.2KLG; its free acid, being referred to as 2KLG).

The 2KLG produced by fermentation is usually present in the form of calcium salt in the fermentation broth, which is produced when a calcium salt added to the broth for controlling the pH value during the fermentation process. This calcium salt is usually separated and purified by conversion into alkali metal salts, particularly the sodium salt, which is insoluble in alcohols (See, for instance, Japanese Patent Publication Nos. 34,799/82 and 34,800/82).

DESCRIPTION OF THE PRIOR ART

2KLG has heretofore been used in the form of acetonide as the starting material for the commercial-scale production of ASA. Utilization of the alkali metal salts of 2KLG, accordingly, has not been investigated sufficiently. Conversion of diacetone 2-keto-L-gulonate monohydrate (hereinafter, referred to as diacetone derivative) into ASA in the prior art can be effected by for instance, heating a mixture of 1 Kg of diacetone derivative, 1.5 L of trichloroethylene, 0.09 L of ethanol and 0.15 Kg of hydrochloric acid (up to 60° C.), wherein the starting material is completely dissolved in the mixture within 20-30 minutes to give a clear solution, which is, thereafter slurried again for a short period of time (5 minutes or so) and the reaction proceeds in the slurry to completion.

Free 2KLG can be converted into ASA in a similar manner as described above without encountering any technical problem. Therefore, as far as an isolation step of the intermediate, 2KLG, is permitted to be included in the process, the ASA can be prepared from an alkali metal salt of 2KLG without any difficulty.

The isolation step is however very expensive and should desirably be avoided in the commercial production of ASA. When the alkali metal salt of 2KLG is slurried in a very small amount of solvent and hydrogen chloride is introduced into the very thick mixture, free 2KLG and alkali metal chloride (hereinafter, referred to as "by-product") are first produced and then the liberated 2KLG turns into ASA with the rise of temperature. Since the solubilities of the alkali metal salt of 2KLG, ASA and the by-product are very poor, no change is observed externally in the thick mixture.

Namely, in the slurry, a composition merely turns into another composition, wherein the by-product is intermingled with the intended product, which is very difficult to separate from the by-product. Although the by-product should be removed prior to the precipitation of the ASA, there is no means for determining whether turbidity of the reaction mixture is attributable to the by-product or to the ASA.

As indicated above, no similar procedure as those applicable to the cases of diacetone derivative and free 2KLG can be followed in the case wherein an alkali metal salt of 2KLG is employed as the starting material and a very small amount of solvent is used for slurry formation.

SUMMARY OF THE INVENTION

The present invention intends to provide an efficient means for preparing L-ascorbic acid from sodium 2-keto-L-gulonate, wherein impurities attributable to the broth of the previous step are effectively removed along with the by-product and the intended product can be obtained in high purity and high yield.

According to the present invention there is provided a process for preparing L-ascorbic acid from sodium 2-keto-L-gulonate which comprises introducing gaseous hydrogen chloride into a mixture of sodium 2-keto-L-gulonate, ethanol and acetone at a temperature of about 25°-75° C. until precipitation of sodium chloride ends, removing the precipitated sodium chloride before L-ascorbic acid begins to crystalize out, maintaining the filtrate or supernatant at a temperature of about 25°-75° C. for a period of 5-100 hours and cooling said filtrate or supernatant to yield crystals of L-ascorbic acid as a final product.

In a preferred mode of embodying the above-mentioned process, said mixture of sodium 2-keto-L-gulonate, ethanol and acetone is composed at a ratio of 1:0.25-1.00:0.5-2.5 by weight and said gaseous hydrogen chloride to be introduced is about 1.5-2.0 moles to 1 mole of sodium 2-keto-L-gulonate.

As previously described, progress of the reaction cannot be ascertained from the appearance of the reaction mixture containing Na.2KLG and no reliable criterion can be established for determining a period during which the by-product should be removed. A simulation experiment was therefore conducted in order to establish the criterion by using 2KLG instead of Na.2KLG on the basis of the following facts.

(1) Both the Na.2KLG and ASA are scarcely soluble in most organic solvents while the 2KLG is soluble.

(2) During the reaction, the liberated 2KLG is gradually converted into ASA with a rise in the temperature of the reaction mixture and coexists with the unchanged 2KLG.

(3) The resultant ASA precipitates in an ethanol/acetone solvent. Thus, the time for removal of NaCl can be confirmed as a change in appearance of the mixture.

As a result of the simulation experiment, it was confirmed that if ASA is combined with 2KLG in a specified mixing ratio in the presence of a very small amount of alcohol/ketone solvent (a specified ratio) under an acidic condition, the mixture dissolves almost completely; in other words, the slurry is converted into a clear solution.

This phenomenon of the complete dissolution depends on the species and mixing ratio of the solvents employed for slurrying the 2KLG, the combining ratio of ASA to 2KLG and the amount of the acid introduced. Accordingly, this phenomenon soon disappears and the mixture turns turbid to give a slurry again with the increase of the relative amount of ASA coming from 2KLG in the mixture.

For instance, if hydrogen chloride is introduced into a mixture composed of 2KLG, ethanol and acetone in a ratio of 1:0.25-1.00:0.5-2.5 by weight, the mixture is suddenly clarified when the amount of the hydrogen chloride introduced reaches 0.5-1.0 mole to one mole of the 2KLG; this clarified state continues for a period of about 3-6 hours and thereafter the ASA begins to precipitate.

The present inventors have now confirmed that this phenomenon can safely be applied to the case wherein the Na.2KLG is present in the mixture in place of the free 2KLG. Namely, if the Na.2KLG is converted into the 2KLG in advance by introducing hydrogen chloride of an amount sufficient for effecting the conversion, the period for removing the by-product can be simulated from the case wherein 2KLG is used.

In the process of the present invention, although a slurry containing Na.2KLG turns into another slurry containing Na.2KLG, 2KLG, ASA and NaCl which cannot be discerned from the former in appearance, it is possible from the result of the above-mentioned simulation experiment to determine when the by-product should be removed from the reaction mixture. Namely, the present inventors have suceeded in establishing reliable criterion for determining the period for removing the by-product and in proving the appropriateness of the criterion in terms of the purity and yield of the intended product as demonstrated in the working examples which will be described later.

During this period, the by-product can easily be removed almost completely from the reaction mixture and the supernatant or filtrate and washings of the salt can subsequently be allowed to react to eventually give ASA in high purity and high yield.

DESCRIPTION OF THE PREFERRED EMBODIMENT

In performing the process of the present invention, it is desirable to use the solvent in an amount as small as possible in the above-described range, so far as it does not deteriorate the operability (the amount should be sufficient for fluidizing the starting material into a slurry which permits easy stirring so that the duration for removal of the by-product continues as long as possible).

By so doing, it is possible to remove the by-product from the reaction mixture and to collect the produced ASA.

Incidentally, if one of the two solvents, namely alcohol and ketone, is used alone, the 2KLG solidifys after the introduction of the acid and the reaction does not proceed. The by-product is inevitably included in the solidified 2KLG to contaminate it.

By the use of a large amount of alcohol as a single solvent, the solidification may be avoided but the reaction proceeds mainly in the direction of esterification to yield 2KLG ester.

One molar ratio of the introduced hydrogen chloride is consumed for neutralizing the Na.2KLG to liberate 2KLG and the remaining HCl serves to promote enolization and lactonization. If the amount of the remaining HCl is less than 0.5 molar ratio, it is insufficient for the purpose.

Furthermore, since the period until the ASA begins to precipitate is unduly shortened, the removal of the by-product becomes difficult.

It is therefore preferable to use 1.5–2.0 molar equivalents of hydrogen chloride as a whole. The use of hydrogen chloride exceeding this amount is unnecessary and disadvantageous from an economical point of view.

In a preferred mode of embodying the present invention, the reaction mixture, after removal of the by-product, may subsequently be allowed to enolization and lactonization followed by addition of a solvent inert to both the 2KL and ASA.

The inert solvent may be exemplified as aromatic hydrocarbons such as benzene, toluene and xylene and halogenated alkanes such as methylene chloride, chloroform and carbon tetrachloride. The addition of these inert solvents has great advantages in improvement of the purity and yield of the produced ASA or in elimination of the impurity, but such an operation is somewhat disadvantageous in lowering the reaction temperature and in delaying the completion of the lactonization reaction.

These disadvantages can however be overcome to some extent by simple means of slightly increasing the pressure on the reaction system, by for instance, maintaining the reaction vessel in a closed state. The inert solvent may be used in an amount as much as one third of the amount of the reaction mixture in the previous step for attaining the above mentioned purpose and recovered after the reaction completion by rectification for being used again.

Addition of small amount of water is also effective for shortening the time required for the lactonization reaction. However, since the added water acts to promote degradation of the produced ASA, an optimum amount of the water to be added should deliberately be fixed in consideration of the balance between the shortening of the time and the lowering of the yield.

In the following description, the present invention will be elucidated in more detail.

EXAMPLE 1

Sodium 2KLG monohydrate (234.15 g) was slurried in a mixture of ethanol (77 ml) and acetone (214 g), into which hydrogen chloride (72.86 g) was introduced under stirring at room temperature.

Then the temperature of the slurry was elevated to 62°–64° C. and the stirring was continued for about 1.5 hours to precipitate sodium chloride, which was removed by filtration and washed with a mixture of ethanol (10.8 ml) and acetone (29.7 g). The washings were combined with the filtrate.

After the combined solution was maintained at 64°–66° C. under stirring for about 13.5 hours, it was cooled to 10° C. under stirring and then stirred further at the same temperature for about 0.5 hour.

Precipitated crystals (ASA) were collected by filtration, washed twice with acetone (100 g) and dried to give 108.0 g of ASA (purity, 97.0%, net amount, calculated from the purity, 104.8 g, yield, 59.5% and conversion rate, 80.5%).

EXAMPLES 2-7

The combined solution prepared in accordance with the former half of Example 1 was treated under the conditions shown in Table 3 below, by addition of an inert solvent (each, 280.7 g) and maintenance at the temperature under stirring. Then the mixture was cooled to about 10°–15° C. and stirred further for about 0.5 hour to precipitate crystals which were washed with acetone (205 g).

The results are summarized in the table.

In each of these examples, the mother liquor, after removal of the first crop of crystals by filtration, was combined with the washing and condensed to about 50 g under reduced pressure (100 mm Hg) to give the second crop of crystals after similar treatment.

In Examples 5 and 6, the steps after the addition of the inert solvent were performed under positive pressure (2.2 Kg/cm$^2$).

TABLE

| Example | 2 | 3 | 4 | 5 | 6 | 7 |
|---|---|---|---|---|---|---|
| Solvent | Methylene chloride | Ethylene chloride | Toluene | Methylene chloride | Methylene chloride | Chloroform |
| Temp. (°C.) | 50 | 63 | 63–66 | 66–68 | 58 | 50 |
| Time (hr.) | 68.5 | 13.5 | 13.0 | 10.0 | 20.0 | 68.5 |
| Conversion rate (%) | 89.3 | 86.0 | 85.3 | 85.4 | 85.0 | 82.6 |
| First crop of crystals | | | | | | |
| Amount (g) | 129.0 | 121.8 | 124.2 | 120.4 | 122.4 | 125.9 |
| Purity (%) | 98.5 | 98.6 | 98.3 | 99.0 | 99.0 | 99.8 |
| Net amount (g) | 127.5 | 120.1 | 122.1 | 120.4 | 122.4 | 125.9 |
| Yield (%) | 72.4 | 68.2 | 69.3 | 68.4 | 69.5 | 71.5 |
| Second crop of Crystals | | | | | | |
| Amount (g) | 16.9 | 13.9 | 12.3 | 19.8 | 18.6 | 13.3 |
| Purity (%) | 98.81 | 97.4 | 97.2 | 97.7 | 97.4 | 99.7 |
| Net amount (g) | 16.7 | 13.6 | 12.0 | 19.4 | 18.1 | 13.2 |
| Yield (%) | 9.5 | 7.7 | 6.8 | 11.0 | 10.3 | 7.54 |
| Overall yield (%) | 81.9 | 75.9 | 76.1 | 79.4 | 79.8 | 79.0 |

What is claimed is:

1. A process for preparing L-ascorbic acid from sodium 2-keto-L-gulonate, comprising the steps of:

introducing gaseous hydrogen chloride in an amount of 1.5–2 moles to 1 mole of sodium 2-keto-L-gulonate into a mixture of sodium 2-keto-L-gulonate, ethanol and acetone wherein the sodium 2-keto-L-gulonate, ethanol and acetone are present at a weight ratio of 1:0.25–1.00:0.5–2.5 and at a temperature of about 25°–75° C. until precipitation of sodium chloride ends;

removing the precipitated sodium chloride before L-ascorbic acid begins to crystallize out;

maintaining the filtrate or supernatant at a temperature of about 25°–75° C. for a period of 5–100 hours; and cooling said filtrate or supernatant to yield crystals of L-ascorbic acid as a final product.

2. The process of claim 1, wherein at least one solvent inert to L-ascorbic acid is added to said filtrate or supernatant at a ratio of 0.5–1.5 by weight.

3. The process of claim 2, wherein said solvent is an aromatic hydrocarbon or a halogenated alkane.

4. The process of claim 3, wherein said solvent is selected from the group consisting of benzene, toluene, xylene, methylene chloride, chloroform and carbon tetrachloride.